(12) United States Patent
Sase (10) Patent No.: US 6,878,866 B2
(45) Date of Patent: Apr. 12, 2005

(54) *EUSTOMA* HAVING DEFORMED PISTIL AND METHOD FOR BREEDING THE SAME (76) Inventor: Noboru Sase, Ninofukuro 76, Tougane-shi, Chiba 283-0052 (JP)

( * ) Notice: Subject to any disclaimer, the term of this patent is extended or adjusted under 35 U.S.C. 154(b) by 0 days.

(21) Appl. No.: 10/210,527

(22) Filed: Aug. 1, 2002

(65) Prior Publication Data

US 2003/0110539 A1 Jun. 12, 2003

(30) Foreign Application Priority Data

Aug. 3, 2001 (JP) ........................................ 2001-236739
Jun. 17, 2002 (JP) ........................................ 2002-175939

(51) Int. Cl.[7] ............................. A01H 5/00; A01H 1/00; A01H 1/02; C12N 5/00; C12N 5/02
(52) U.S. Cl. ..................... 800/323; 800/260; 800/295; 800/298; 435/430; 435/430.1
(58) Field of Search ................................. 800/323, 298, 800/295, 260; Plt./263

(56) References Cited

FOREIGN PATENT DOCUMENTS

| JP | 02-242764 | 9/1990 |
| JP | 07-170870 | 7/1995 |
| JP | 08-104601 | 4/1996 |
| JP | 08-198704 | 8/1996 |
| JP | 09-012401 | 1/1997 |
| JP | 09-107829 | 4/1997 |
| JP | 09-107831 | 4/1997 |
| JP | 10-150853 | 6/1998 |
| JP | 2000-004701 | 1/2000 |
| JP | 2000-342093 | 12/2000 |

OTHER PUBLICATIONS

Harbaugh et al. 'Florida Blue' Semi–dwarf Lisianthus [Eustoma grandiflorum (Raf.) Shinn.] HortScience 31(6):1057–1058. 1996.*

* cited by examiner

*Primary Examiner*—Andrew Wang
*Assistant Examiner*—June Hwu
(74) *Attorney, Agent, or Firm*—Fish & Richardson P.C.

(57) ABSTRACT

The present invention relates to a novel *Eustoma* having a deformed pistil, the stigma of which does not substantially open, and a method for breeding the same. The *Eustoma* has almost no possibility of being pollinated in a natural condition, thereby have an extremely good flowering period when compared with the conventional *Eustoma*.

23 Claims, 8 Drawing Sheets

Examination Criteria for Classification of Variety Features of Toruko Gikyo

Character 44. Shape of pistil normal    small    mulformed

Shape of pistil

Shape of deformed pistil of the present invention

FIG.1

Examination Criteria for Classification of Variety Features of Toruko Gikyo

Character 44. Shape of pistil

Shape of deformed pistil of the present invention

Top view

Side view

Right: a deformed pistil

Left: a normal pistil having an opened stigma

Schematic diagram of flower.

EUSTOMA HAVING DEFORMED PISTIL AND METHOD FOR BREEDING THE SAME

BACKGROUND OF THE INVENTION

1. Field of the Invention

The present invention relates to a novel *Eustoma* having a deformed pistil, the stigma of which does not substantially open, and a method for breeding the same. More specifically, it relates to a novel *Eustoma* having a deformed pistil, the stigma of which does not open even after the flower perishes and has almost no possibility of being pollinated in a natural condition, thereby having an extremely good flowering period, and a method for breeding the same.

2. Description of the Related Art

*Eustoma* is a self-reproducing seed plant of Gentianaceae *Eustoma*, which is native to North America, and is well known as Toruko Gikyo in Japan. Presently, breeding of *Eustoma* for use as a cut flower or horticultural flower has been progressing, and plants having various colors and shapes are on the market. Such a *Eustoma* as a commercial product requires not only fineness of flower color or shape, but also preservation of freshness after shipment.

Generally, it is known that, after *Eustoma* come into flower, pollination accelerates aging of the flower and so the appreciation period becomes shorter. Thus, in order to frustrate pollination, refinements have been made, such as positioning an anther of a stamen lower than the position of a stigma so as to maintain a long flowering period.

Known techniques relating to *Eustoma*, include a method of producing a pure line *Eustoma* in a short time by using pseudofertilized ovule culture or hyperploidy pollen (Japanese Patent Application Laying-Open (Kokai) Nos. 2000-4701 and 2000-342093, a method of efficiently producing a Toruko Gikyo F1 hybrid by introduction of a male-sterile gene (Japanese Patent Application Laying-Open (Kokai) No. 9-107829, a method involving in efficient rooting by using callus culture (Japanese Patent Application Laying-Open (Kokai) No. 9-107831), and a method of efficiently producing a stunted Toruko Gikyo by adventitious embryo formation. (Japanese Patent Application Laying-Open (Kokai) No. 7-170870), but there are no reports regarding a deformed pistil or improvement in flowering period.

Method generally used to improve flowering period of a plant, include methods of controlling the outer environment of a plant, such as environmental management during distribution, or use of an agent. For example, there are known some devices and agents including a preserving device containing pressurized nonpolar gas (Japanese Patent Application Laying-Open (Kokai) No. 8-104601), a thermoregulated preserving device (Japanese Patent Application Laying-Open (Kokai) No. 10-150853), a buffer device for transporting flowers while carbon dioxide generates (Japanese Patent Application Laying-Open (Kokai) No. 2-242764), an agent for retaining the freshness of cut flowers (there exist many publications such as Japanese Patent Application Laying-Open (Kokai) Nos. 9-12401 and 8-198704), etc.

On the other hand, as a method for directly manipulating a plant itself, there has been attempted a method for improving flowering period by making a triploid plant or male-sterile plant, thereby controlling the reproductive function of the plant.

However, in general, high costs are required to control the outer environment and the effect has a certain limit. Moreover, there has been a problem that a triploid or male-sterile plant is poor in productivity because it cannot have a seed.

SUMMARY OF THE INVENTION

It is the object of the present invention to provide a *Eustoma* having an excellent flowering period.

While crossing known *Eustoma* varieties and making selections to establish a variety having a good flower color, flower shape and flowering period, the present inventors, by sheer coincidence, have obtained a novel *Eustoma* having a deformed pistil, which differs from the conventional pistil. The stigma of the deformed pistil is characterized in that it does not open even after the flower perishes and so is not pollinated. Accordingly, aging of the flower due to pollination is less likely to occur, and reproductive function after flowering is regulated. Therefore, the novel *Eustoma* was found to have an extremely good flowering period when compared with the conventional *Eustoma*. Moreover, the present inventors have also found that this character can be fixed to a certain extent by allowing artificial self-pollination by opening the stigma using a pair of tweezers, or by crossing between *Eustoma* plants having a deformed pistil by a similar operation, so that seed reproduction is also possible, thereby completing the present invention.

That is to say, the present invention relates to a *Eustoma* having a deformed pistil, a stigma of which does not substantially open. It is preferable that the flowering period of the *Eustoma* is extended by 10% or more when compared with a *Eustoma* having a normal pistil.

Moreover, the present invention relates to a method for breeding the above-described *Eustoma*, which comprises crossing a *Eustoma* variety "Himemidori I" as a male parent with a *Eustoma* variety "Hohoemi I" as a female parent, and selecting a *Eustoma* having a deformed pistil, and a method for breeding the above-described *Eustoma*, which further comprises allowing the obtained *Eustoma* having a deformed pistil to artificially self-pollinate.

Furthermore, the present invention relates to a method for breeding a *Eustoma* having a deformed pistil by crossing the above-described *Eustoma* having a deformed pistil with a *Eustoma* not having a deformed pistil or another *Eustoma* having a deformed pistil.

Still further, the present invention relates to a seed of the above-described *Eustoma* having a deformed pistil.

DETAILED DESCRIPTION OF THE PREFERRED EMBODIMENTS

The present invention will be explained in detail below.

1. *Eustoma* Having Deformed Pistil

The "*Eustoma*" of the present invention is a plant of Gentianaceae *Eustoma*, and it is a flower belonging to *Eustoma grandiflorum* or *Eustoma exaltatum*, which is familiar to us in Japan by the Japanese name, "Toruko Gikyo".

Figure 8:
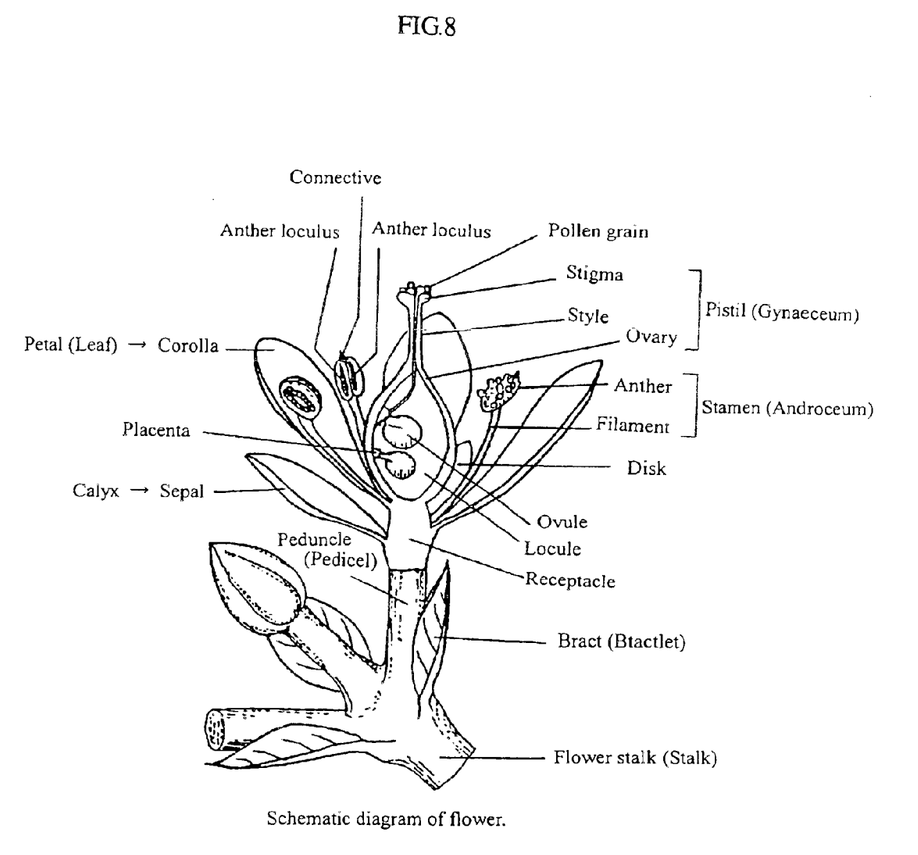
FIG. 8 is a schematic diagram showing the structure of a flower.

Generally, a flower including *Eustoma* has a green sepal and a beautiful petal (a leaf), and further has a stamen (androceum) and a pistil (gynaeceum) therein. A typical pistil consists of three parts such as a stigma, a style and an ovary, and among these, a stigma and an ovary are essential for pollination and fertilization (refer to FIG. 8).

The "stigma" is a surface part of the pistil where pollination is performed, and in general it is located at the edge of the style. The stigma has a shape specific for the genus or species, and examples of shape include punctate, linear, capitate, sheet, discoideus, beak shaped, etc. The stigma of a mature pistil has a mechanism adapted to pollination, in that the stigma secretes mucus, has a projection, is divided, or in some cases, it moves due to contact stimulus and engulfs a pollen grain.

In the case of *Eustoma*, the stigma part of a mature pistil opens (cleaves), and a pollen attaches to the part opened. Therefore, it is essential for fertilization of a *Eustoma* that the stigma opens.

Figure 1:
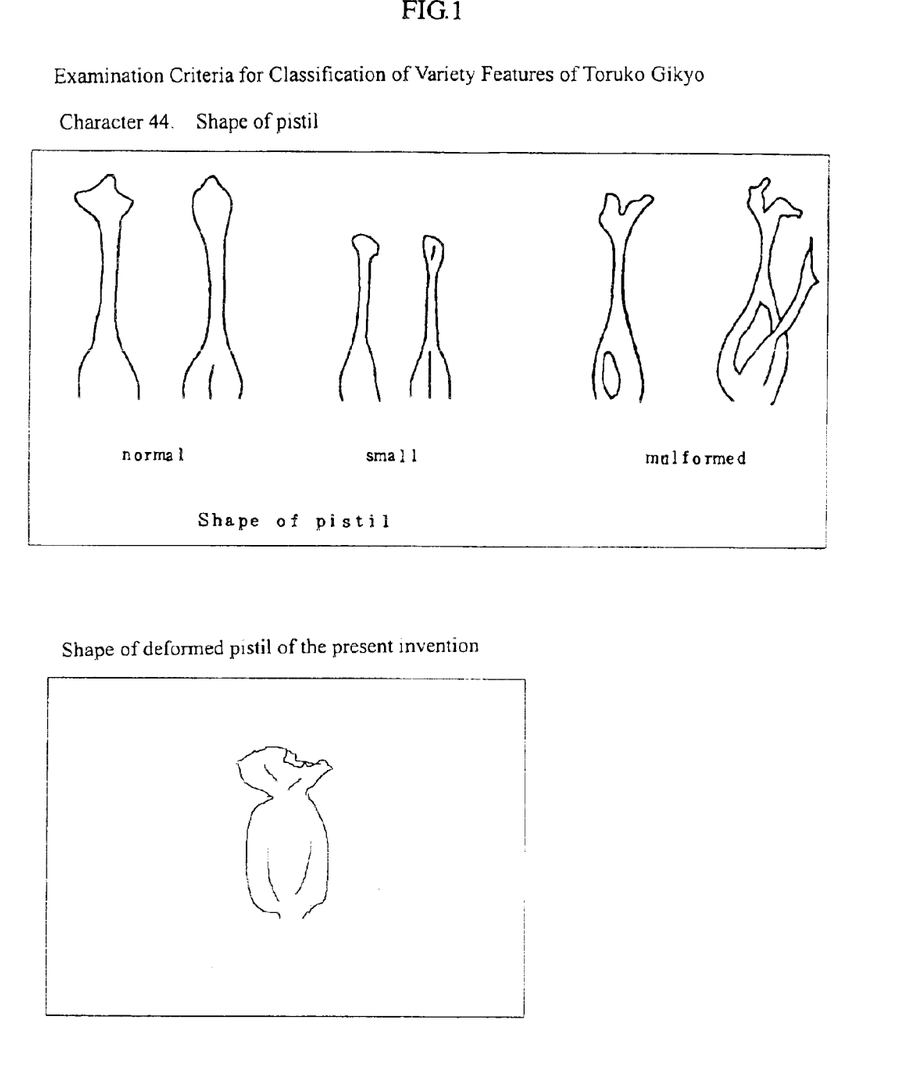
FIG. 1 shows the shape of a pistil shown in "Examination Criteria for Classification of Variety Features of Toruko Gikyo" and the shape of the deformed pistil of the present invention.

The "deformed pistil" of the present invention differs from the pistil of the conventional *Eustoma* in respect of appearance and function, and it has the following features:

(1) the present deformed pistil has a shape completely different from a normal pistil, a small pistil and a malformed pistil which are shown in "shape of pistil, character 44, Examination Criteria for Classification of Variety Features of Toruko Gikyo", which is submitted for registration of the variety according to the Seeds and Seedling Law (revised in 1998) (see FIG. 1.)

(2) the present deformed pistil has a stigma which does not substantially open in a natural condition even after the flower perishes.

(3) the character is dominantly inherited.

(4) a *Eustoma* having the present deformed pistil has a longer flowering period than a *Eustoma* having a normal pistil.

The term "stigma does not substantially open" is used in the present invention to mean that even if a part of the stigma slightly opens, there is almost no possibility of being pollinated in a natural condition, or by operation after collection of flowers or vibration during transportation. That is to say, the pistil of a plant opens its stigma part after coming into flower so that it is ready to be pollinated. However, a deformed pistil, the stigma of which does not substantially open, has almost no possibility of being pollinated in a natural condition, and so ovule development or seed formation following pollination is unlikely to occur. It is a good reason for the long flowering period brought from the *Eustoma* of the present invention that the aging of a flower due to pollination is retarded by such a regulation of a reproductive function.

2. Method for Breeding *Eustoma* Having Deformed Pistil

The character and history of the *Eustoma* used in the method for breeding a *Eustoma* having a deformed pistil of the present invention are as follows.

Male (Pollen) Parent "Himemidori I"

Character: A small green circular flower having a thick petal. The pistil is normal.

History: For the purpose of obtaining a green flower, using a *Eustoma* having a small greenish white circular flower blooming at a farm owned by the present inventor as a female (pistillate) parent and a green *Eustoma* purchased at Tokyo Ota Flowers and Ornamental Plants Market as a male parent, these *Eustoma* plants were repeatedly subjected to crossing and selections were made over 4 generations so as to fix the character. The thus obtained seed was deposited with the National Institute of Advanced Industrial Science and Technology, an Independent Administrative Institution under the Ministry of Economy, Trade and Industry, AIST (Tsukuba Central 6, Higashi 1-1-1, Tsukuba, Ibaraki, Japan) under accession No. FERM BP-8074 (a request to transfer from the original deposition [FERM P-18441 deposited on Jul. 30, 2001] to a deposition under the terms of the Budapest Treaty was accepted on Jun. 13, 2002).

Female (Pistillate) Parent "Hohoemi I"

Character: An apricot pink-colored flower having a fringe on a petal thereof. The pistil is normal.

History: For the purpose of obtaining an apricot pink-colored flower having a beautiful fringe, using a cream *Eustoma*[*1] having a fringe on a petal thereof appearing in a farm owned by the present inventor as a female parent and a pink *Eustoma* having a fringe on a petal thereof appearing from Skyfriend[*2] of Miyoshi & Co., Ltd. as a male parent, these *Eustoma* plants were repeatedly subjected to crossing and selection so as to fix the character. The final fixed rate was 80%. This variety was not registered and so the seeds are not conserved at present.

[*1] The character of the pistillate parent was fixed later and the variety was registered in the name of "Fufu cream" (Variety Registration No. 7046, registered Mar. 16, 1999).

[*2] A *Eustoma* having a white and blue picoty petal, which was being sold by Miyoshi & Co., Ltd. when the breeding was carried out (around year 1986). This *Eustoma* is not on sale at present.

The term "self-pollination" regarding the breeding method of the present invention is used to mean that a pollen from the same flower of the same stock is attached to the stigma of a pistil or that a pollen from another flower of the same stock is attached thereto. In order to allow the *Eustoma* having a deformed pistil of the present invention, the stigma of which does not substantially open in a natural condition, to self-pollinate, it is necessary to "allow to artificially self-pollinate".

The term "allow to artificially self-pollinate" is used herein to mean that self-pollination is carried out by adding some kind of artificial operation of opening the stigma of a pistil or the upper part of the stigma by a pair of tweezers. However, it is not limited to the term "pollination (attachment of pollen onto the stigma)" to such an extent that it is an action capable of formation of a seed by fertilization between an sperm nucleus and an egg cell following the pollination.

Various types of "*Eustoma* plants having a deformed pistil" which have different flower shape, flower color, petal, etc., can be bred by crossing the *Eustoma* having a deformed pistil of the present invention with another *Eustoma*. As stated above, since the character of the deformed pistil in the present invention is dominantly inherited, a *Eustoma* to be crossed with the *Eustoma* of the present invention may be either a *Eustoma* having a deformed pistil or *Eustoma* not having a deformed pistil. Moreover, both of the *Eustoma* of the present invention and the *Eustoma* to be crossed with the *Eustoma* of the present invention may be used as a female parent or male parent. However, where the *Eustoma* having a deformed pistil of the present invention is used as a male parent and a *Eustoma* not having a deformed pistil as a female parent for crossing, there is no need to allow to artificially self-pollinate, and accordingly it is more preferable. The thus obtained *Eustoma* has a deformed pistil, and therefore it has an excellent character in that it has a good flowering period.

3. Test of Flowering Period

Evaluation of the flowering period of the *Eustoma* having a deformed pistil of the present invention can be carried out as follows. It should be noted that the term "flowering period" in the present specification is used to mean "maintenance of the flower opened", and accordingly the term "good flowering period" is used to mean that "a flowering period from the beginning of flowering to the end of flowering is relatively long". Whether or not the flowering period is relatively long is determined by a comparative evaluation of a multiple number of *Eustoma* having a normal pistil and *Eustoma* having a deformed pistil under the same environmental conditions.

Where considering a flower (*Eustoma*) especially as a commercial product, such a flower is collected from a field, subjected to selection, packed in a box for delivery, transported by car or the like, and sold in a market or the like. After a consumer buys the flower, it is subjected to appreciation for a certain period. That is to say, the flower is required to retain the character of having a good flowering period both in a period from collection of the flower to arrival at a consumer and a period when the consumer appreciates it.

As an example of a flowering period test, a method for evaluating the flowering period of a cut flower will be explained. By this method, first, as test materials, from among *Eustoma* plants cultivated under the same conditions, an appropriate number of *Eustoma* having a normal pistil and *Eustoma* having a deformed pistil are prepared, respectively. On the day of flowering (the day when anther dehiscence is observed), flowers are almost simultaneously collected from each *Eustoma* with the peduncle of each flower remaining thereon, and then the peduncle part is controlled at a certain length (e.g. about 4 to 6 cm).

Subsequently, while a cross section of a stem of the thus prepared test materials is immersed in water, the test materials are left in a constant temperature room, which has a constant temperature (preferably 18° C. to 22° C.), a constant humidity (preferably 55% to 65%) and a light cycle and a dark cycle are shifted every 12 hours, and the change of the appearance of flowers is observed.

The "beginning of flowering" is defined as a time when anther dehiscence is observed, whereas the "end of flowering" is decided and determined from the appearance of a petal (the wrinkle or wilting of a petal), so that the flowering period of a flower (a period from the beginning of flowering to the end of flowering) under the above-described conditions is determined. The flowering period of the *Eustoma* having a deformed pistil of the present invention can be evaluated by determining the average value of the determined flowering period of each of a *Eustoma* having a deformed pistil and a *Eustoma* having a normal pistil, and making a comparison.

The *Eustoma* having a deformed pistil of the present invention has a longer flowering period than that of a *Eustoma* having a normal pistil by at least 10% or more, preferably 20% or more, and more preferably 25% or more.

EXAMPLES

The present invention will be further described in the following examples. The examples are provided for illustrative purposes only, and are not intended to limit the scope of the invention.

Example 1

Breeding of *Eustoma* Having Deformed Pistil

Breeding of a *Eustoma* having a deformed pistil was carried out from 1991 to 1997 at an address, 76 Ninofukuro, Togane-shi, Chiba-ken, which was a field owned by the present inventor.

(1) Breeding of Male Parent

For the purpose of obtaining a green flower, using a *Eustoma* having a small greenish white circular flower blooming at a farm owned by the present inventor as a female parent and a *Eustoma* having a green flower purchased at Tokyo Ota Flowers and Ornamental Plants Market as a male parent, these *Eustoma* plants were crossed by a common method and selections were made over 4 generations so as to almost fix the character. The pistils of the parents were normal, but some deformed pistils appearing in this breeding process. However, the shape of a pistil was not an item as a selection standard in the breeding process. The thus fixed *Eustoma* had a normal pistil, and had a small green circular flower having a thick petal. The obtained *Eustoma* was called "Himemidori I" by the present inventor.

(2) Breeding of Female Parent

For the purpose of obtaining an apricot pink-colored flower having a beautiful fringe, using a cream *Eustoma* having a fringe on a petal thereof appearing in a farm owned by the present inventor as a female parent and a pink *Eustoma* having a fringe on a petal thereof appearing from Skyfriend of Miyoshi & Co., Ltd. as a male parent, these *Eustoma* plants were repeatedly subjected to crossing and selection by a common method so as to fix the character. The pistils of the parents were normal.

The obtained *Eustoma*, as with the parents, had a fringe on an apricot pink-colored petal thereof, and was called "Hohoemi I" by the present inventor. The pistil was normal.

(3) In 1996, for the purpose of establishing a *Eustoma* variety having green flower color and a fringe on a petal thereof, using the above-described "Himemidori I" as a male parent and the above-described "Hohoemi I" as a female parent, both plants were crossed and the obtained seeds were sowed. As a result, *Eustoma* plants, flower color of which was brown and had a fringe on a petal thereof, and further had a deformed pistil whose appearance was clearly different from the previous pistil, appeared at a ratio of 2 stocks for all 200 stocks.

(4) It was found that this deformed pistil had a stigma which did not open in a natural condition even after the flower perished, and accordingly had almost no possibility of being pollinated in a natural condition. Moreover, it was also found that a *Eustoma* having this deformed pistil had an extremely good flowering period when compared with a *Eustoma* having a normal pistil.

Figure 2:
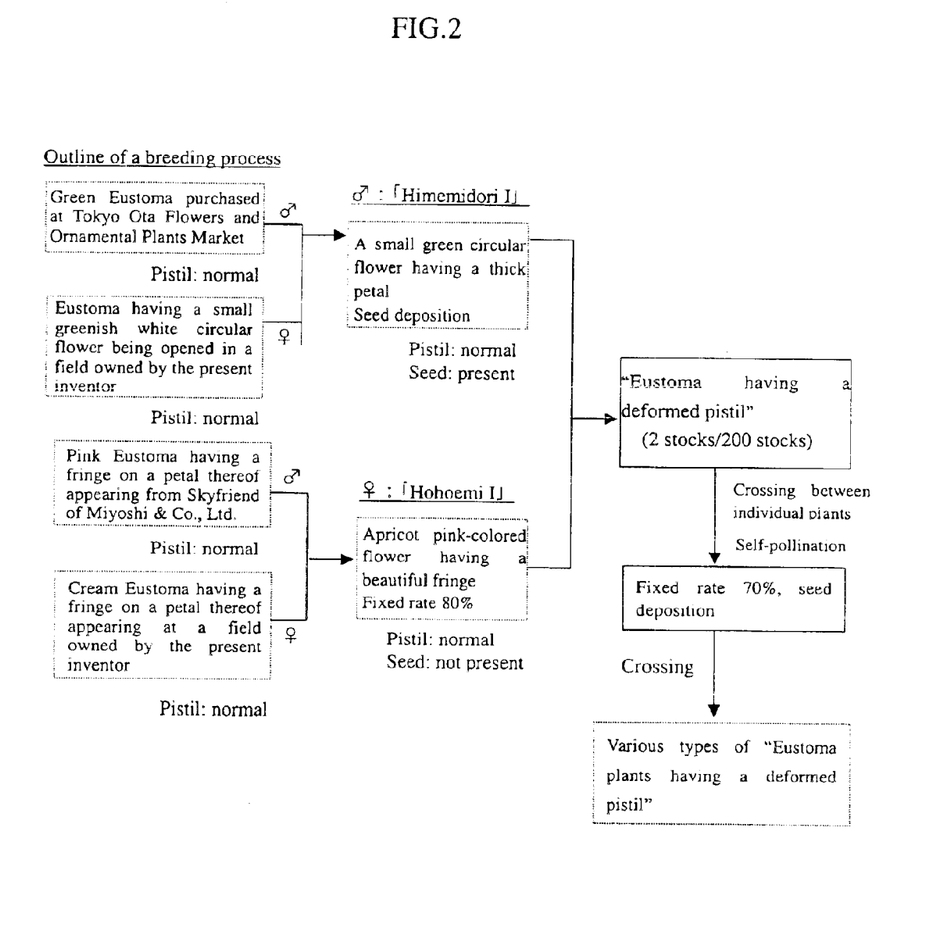
FIG. 2 shows the outline of the breeding process of the present invention.
Figure 3:
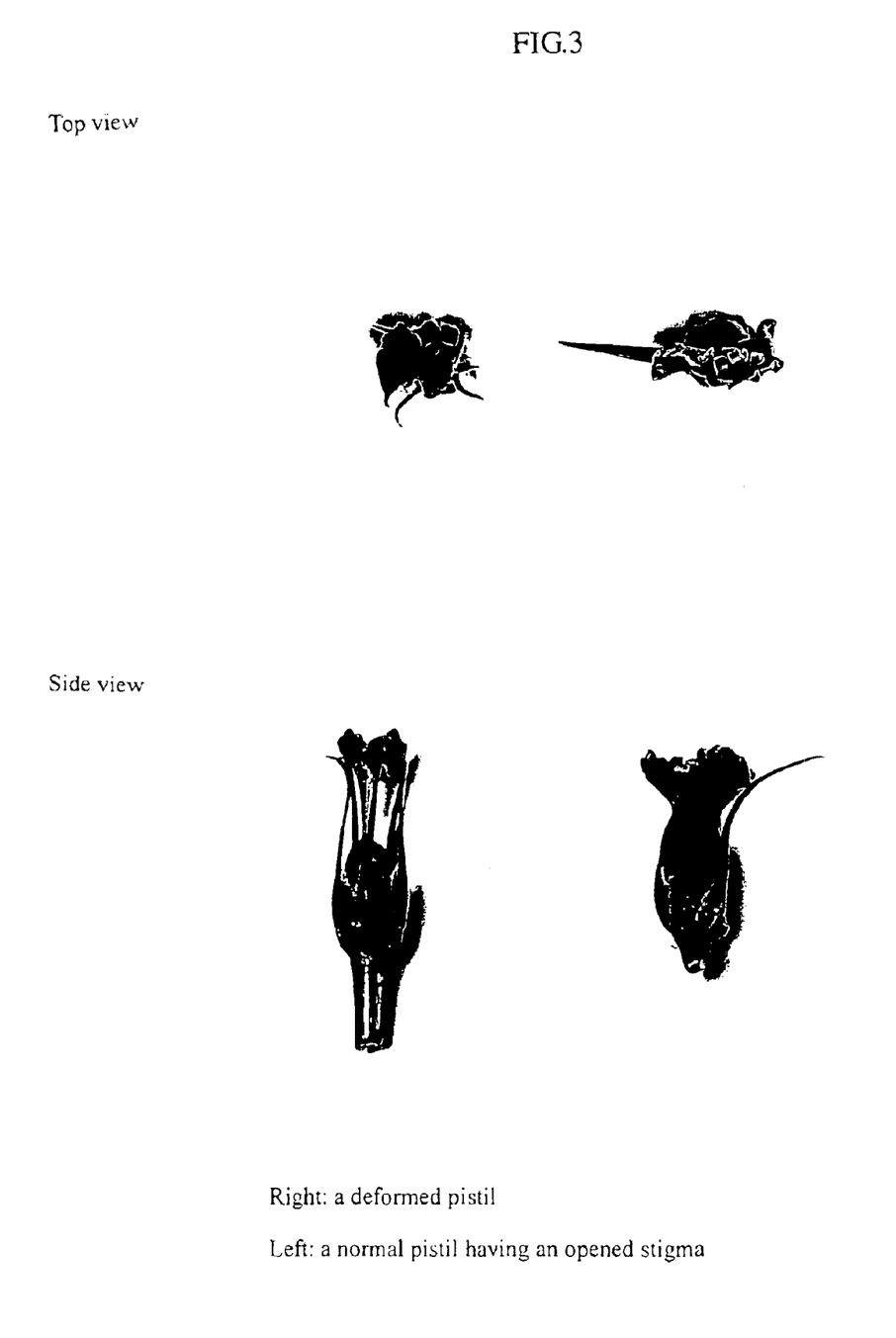
FIG. 3 is a photograph for comparing the deformed pistil of the present invention and a normal pistil.
Figure 4:
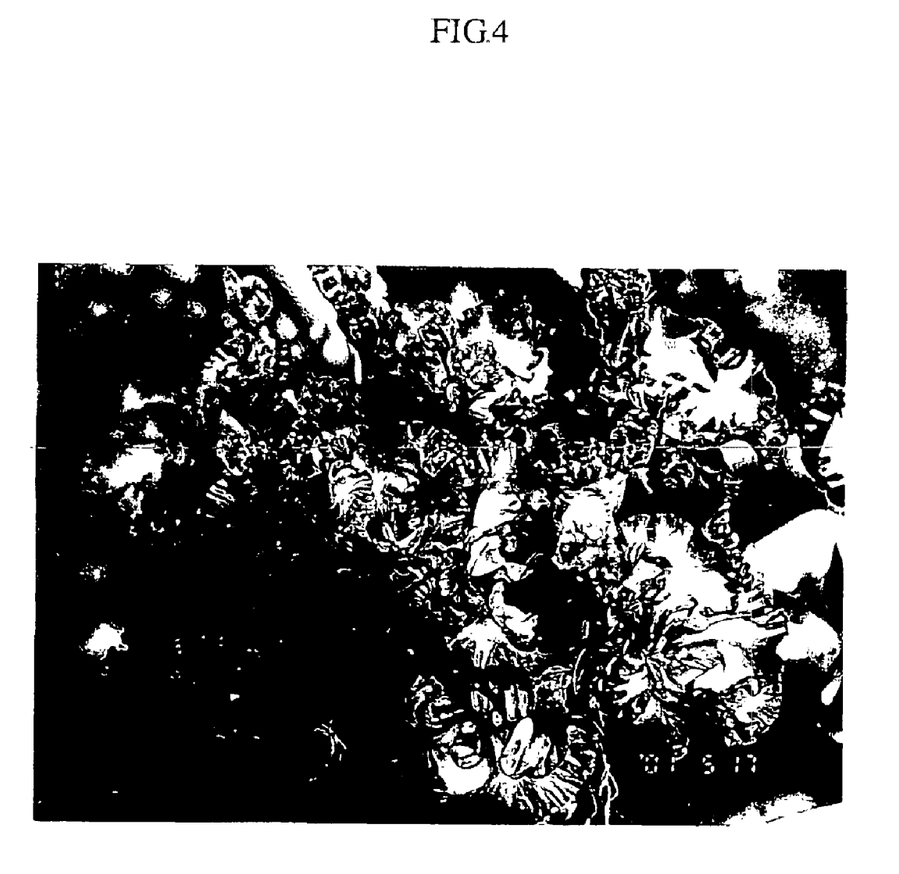
FIG. 4 is a photograph of the *Eustoma* having a deformed pistil of the present invention.

It should be noted that cultivation conditions such as sowing and dressing in the breeding process were equivalent to common cultivation conditions for *Eustoma*, and no particular conditions were provided. An outline of the above breeding process is shown in FIG. 2.

Example 2

Fixing of *Eustoma* Having Deformed Pistil

Fixing of the *Eustoma* having a deformed pistil obtained in Example 1 was attempted. The fixing was carried out from 1996 to 2001 at an address, 76 Ninofukuro, Togane-shi, Chiba-ken, which was a field of the present inventor.

(1) The *Eustoma* having a deformed pistil obtained in Example 1 had a stigma which did not open in a natural condition, and so could not be pollinated. Thus, the pistil was opened using a pair of tweezers, and pollen from the same flower was applied thereto to allow it to artificially self-pollinate.

(2) *Eustoma* plants were cultivated from the seeds obtained by the self-pollination, and *Eustoma* plants having a deformed pistil were selected from among these plants. Then, self-fertilization or crossing between individual plants was further carried out.

(3) In a process of repeating the above step, there were mainly obtained *Eustoma* plants having a deformed pistil, which had three different flower colors such as purple, brown and green. Each color had light and shade, and some flowers had a bicolored petal.

(4) Finally, the seed of a "*Eustoma* having a deformed pistil, the flower color of which is brown and has a fringe on a petal thereof", which had the highest fixed rate (fixed rate 70%), was deposited with the National Institute of Advanced Industrial Science and Technology, an Independent Administrative Institution under the Ministry of Economy, Trade and Industry, AIST (Tsukuba Central 6, Higashi 1-1-1, Tsukuba, Ibaraki, Japan) under accession No. FERM BP-8075 (a request for transferring from the original deposition [FERM P-18442 deposited on Jul. 30, 2001] to a deposition under the terms of the Budapest Treaty was accepted on Jun. 13, 2002).

Example 3

Breeding of Various Types of "*Eustoma* Plants Having Deformed Pistil"

The *Eustoma* having a deformed pistil fixed in Example 2 was crossed with another *Eustoma* so that breeding of various types of "*Eustoma* plants having a deformed pistil" was attempted. Breeding was carried out from 1997 to 2001 at an address, 76 Ninofukuro, Togane-shi, Chiba-ken, which was a field of the present inventor.

(1) By a method of opening a deformed pistil using a pair of tweezers and allowing artificial self-pollination, a *Eustoma* having a deformed pistil can be obtained with reliability, but this method requires much expense in time and effort. Hence, to obtain a *Eustoma* having a deformed pistil efficiently, the pollen of the *Eustoma* having a deformed pistil fixed in Example 2 was applied to the pistil of the *Eustoma* having a normal pistil. As a result, it was found that a *Eustoma* having a deformed pistil was obtained at an almost constant ratio.

Figure 5:
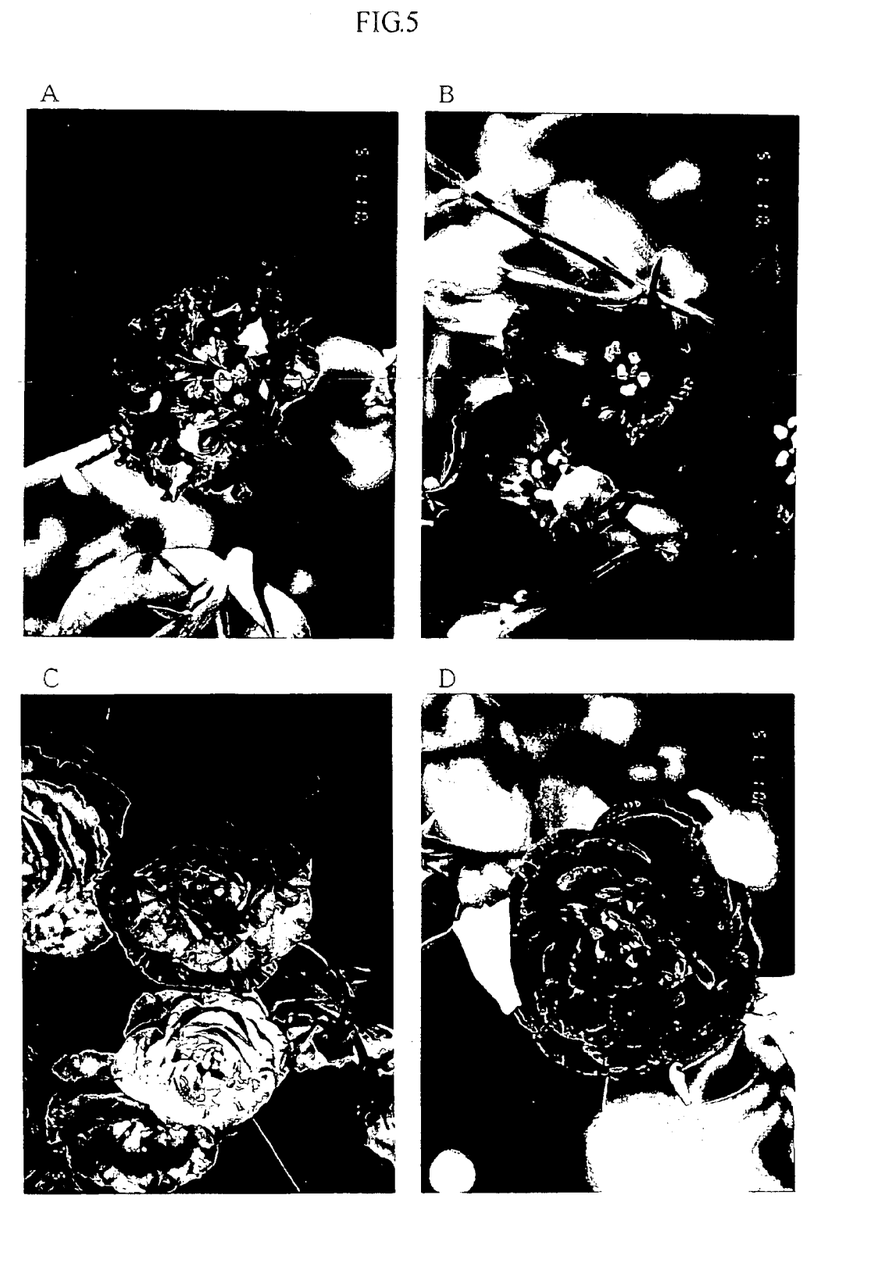
FIG. 5 are photographs of various types of "*Eustoma* flowers having a deformed pistil", which were obtained by crossing a *Eustoma* having a deformed pistil with a *Eustoma* having a normal pistil.
Figure 6:
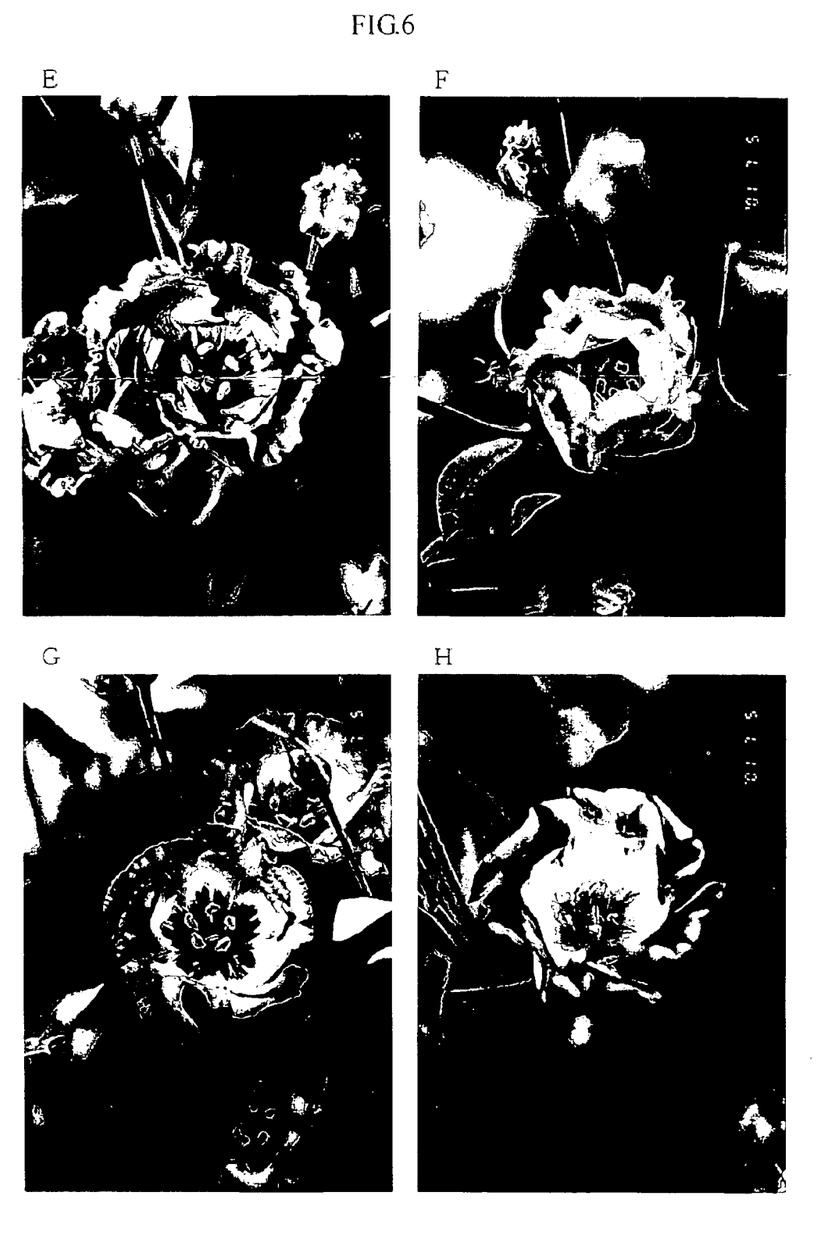
FIG. 6 are photographs of various types of "*Eustoma* flowers having a deformed pistil", which were obtained by crossing a *Eustoma* having a deformed pistil with a *Eustoma* having a normal pistil.

(2) Thus, as shown in Table 1, *Eustoma* plants having a deformed pistil were crossed with *Eustoma* plants having a normal pistil to obtain various types of "*Eustoma* plants having a deformed pistil" (A to H). The photographs of the obtained *Eustoma* plants are shown in FIG. 5 (A to D) and FIG. 6 (E to H).

TABLE 1

| Pistillate parent | | × | Pollen parent | | The obtained Eustoma | | |
|---|---|---|---|---|---|---|---|
| (Normal pistil; | Small rose circular,) Fringe | × | (Deformed pistil;) | Brown) | (Deformed pistil; | Light Brown, Fringe | A |
| (Normal pistil; | Purple) | × | (Deformed pistil; | Purple) | (Deformed pistil; | Purple | B |
| (Normal pistil; | White, Double flowered) | × | (Deformed pistil; | Brown, Single) flowered | (Deformed pistil; | White Brown, Double flowered | C |
| (Normal pistil; | Yellow, Double) flowered | × | (Deformed pistil; | Brown, Single) flowered | (Deformed pistil; | Purple, Double flowered | D |
| (Normal pistil; | Green, Fringe) | × | (Deformed pistil; | Green/White Bicolor) | (Deformed pistil; | Brown, Multiple circular rings, Fringe | E |
| (Normal pistil; | Green) | × | (Deformed pistil; | Green) | (Deformed pistil; | Green | F |
| (Normal pistil; | Green) | × | (Deformed pistil; | Green) | (Deformed pistil; | Brown, Multiple circular rings | G |
| (Normal pistil; | Blue picotee, Multiple) circular rings | × | (Deformed pistil; | Purple/Green Bicolor) | (Deformed pistil; | Purple/White/Green | H |

Figure 7:
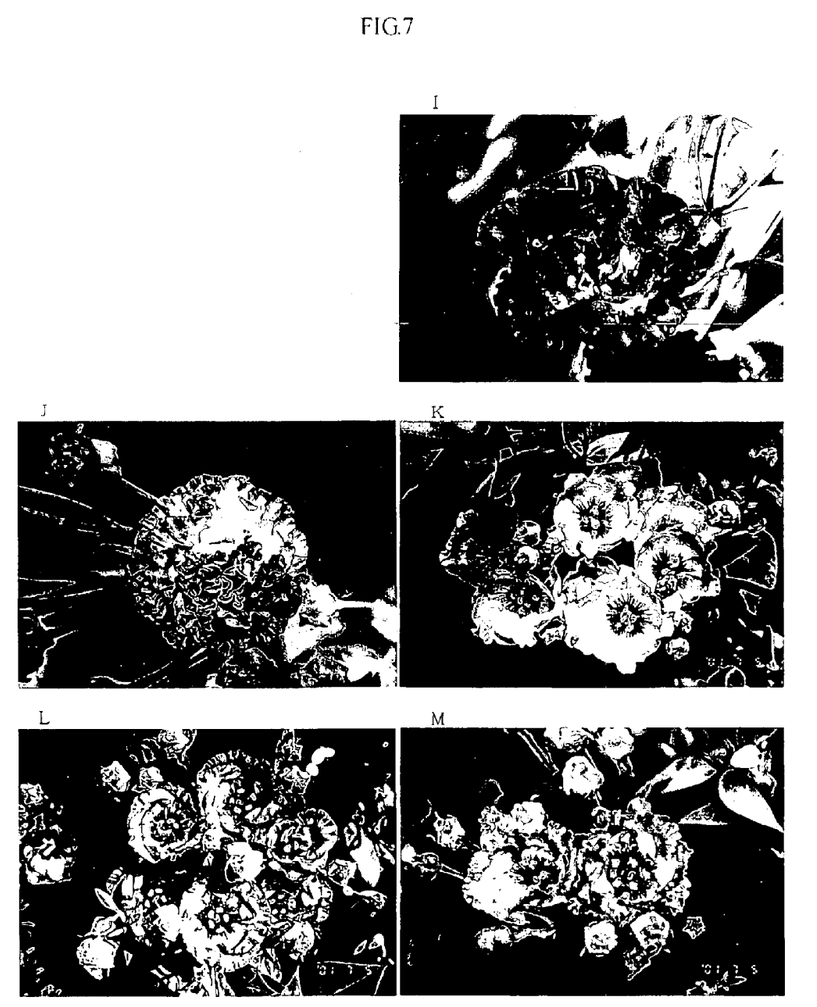
FIG. 7 is a group of photographs of various types of "*Eustoma* flowers having a deformed pistil" described in Example 3-(3).

(3) Moreover, the "*Eustoma* plants having a deformed pistil" obtained in (2) above were subjected to self-pollination or crossing between individual plants to obtain a group of *Eustoma* plants having a deformed pistil (I to M). Photographs of the obtained *Eustoma* group (I to M) are shown in FIG. 7.

Example 4

Genotype of Deformed Pistil

To examine the genotype of a deformed pistil, the following test was carried out.
(1) First, a *Eustoma* having a deformed pistil was subjected to self-pollination and the obtained seeds were sowed.
(2) Next, *Eustoma* plants having a deformed pistil were selected from among the thus obtained plants, self-pollinated and then subjected to selection of lines. As a result of a progeny test, it was found that all were *Eustoma* plants having deformed pistils (lines assumed to have the homologous genotype of a deformed pistil and hereinafter referred to as a "deformed pistil (homo)").
(3) Then, this "deformed pistil (homo)" was subjected to self-pollination or crossing with a *Eustoma* (a female parent) having a normal pistil. As shown in Table 2, deformed pistils were obtained in all cases.

TABLE 2

Appearance rate of deformed pistil

|  | Deformed pistil stock | Normal pistil stock | Number of stocks examined |
|---|---|---|---|
| Self-pollination of deformed pistil (homo) | 100 | 0 | 100 |
| Deformed pistil (homo) × Normal pistil | 100 | 0 | 100 |

Example 5

Test of Flowering Period (1) Test Materials

Two types of *Eustoma* plant were used as test materials: [1] *Eustoma* plants having a normal pistil from among individuals appearing from crossing *Eustoma* plants (female parents) having a normal pistil with *Eustoma* plants (male parents) having a deformed pistil, and [2] *Eustoma* plants having a deformed pistil from among individuals appearing from crossing *Eustoma* plants (female parents) having a normal pistil with *Eustoma* plants (male parents) having a deformed pistil.

The above two types of *Eustoma* plants were obtained by collecting *Eustoma* flowers with the peduncles remained, which were likely to open at the same day, from a field for cultivating *Eustoma*, and controlling the peduncle part at a length of 4 cm. Using the thus prepared *Eustoma* flowers, the test was carried out, while setting the number of flowers at 32 (n=32).

(2) Test Method

The test materials were inserted into holes set at 8 cm intervals lengthwise and breadthwise on a 2 cm-thick styrofoam piece, and then the styrofoam piece was floated on a tray filled with tap water. The flowering period test was carried out in a constant temperature room where the temperature was 20° C., the humidity was 60% (±5%) and a common fluorescent lamp (Eyeline white light rapid 40W) was switched on or off every 12 hours. Since contamination of water was not particularly observed during the test, exchange of water was not carried out.

(3) Evaluation and Determination

The "beginning of flowering" was defined as a time when anther dehiscence was observed, whereas the "end of flowering" was decided and determined by a technician, who bred the flowers and observed the appearance of a petal and the wrinkle or wilting of a flower.

(4) Test Results

As a result, it was found that a *Eustoma* having a deformed pistil has a flowering period that is longer than that of a *Eustoma* having a normal pistil by about 3 or 4 days on average (Table 3).

TABLE 3

Results of flowering period test regarding deformed pistil

| Reference No. | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| Normal pistil | 16 | 10 | 10 | 12 | 12 | 15 | 15 | 16 | 11 | 11 | 11 | 11 | 14 | 16 | 16 | 15 |
| Deformed pistil | 18 | 18 | 18 | 17 | 16 | 16 | 17 | 15 | 18 | 18 | 17 | 18 | 16 | 14 | 18 | 15 |

| Reference No. | 17 | 18 | 19 | 20 | 21 | 22 | 23 | 24 | 25 | 26 | 27 | 28 | 29 | 30 | 31 | 32 | Total | Average (day) |
|---|---|---|---|---|---|---|---|---|---|---|---|---|---|---|---|---|---|---|
| Normal pistil | 10 | 15 | 13 | 11 | 10 | 15 | 10 | 11 | 16 | 15 | 13 | 12 | 11 | 15 | 11 | 14 | 202 | 12.6 |
| Deformed pistil | 15 | 16 | 17 | 16 | 15 | 15 | 15 | 15 | 18 | 17 | 15 | 17 | 15 | 16 | 16 | 15 | 253 | 15.81 |

According to the present invention, there is provided a *Eustoma* having a deformed pistil, the stigma of which does not substantially open. The flowering period of this *Eustoma* can be retained for a long time without using a special device or freshness preserving agent. Further, by crossing the present *Eustoma* with another *Eustoma* as appropriate, it is possible to change flower shape, flower color and the form of a petal to those suitable for the needs of consumers and it is also possible to obtain a seed. Accordingly, a *Eustoma* having a high commercial value is provided.

What is claimed is:

1. A *Eustoma* seed, deposited under Accession No. FERM BP-8075.
2. A *Eustoma* plant, or its parts, produced by growing the seed of claim 1.
3. Pollen of the *Eustoma* plant of claim 2.

4. An ovule of the *Eustoma* plant of claim 2.

5. A *Eustoma* plant, or parts thereof, having all of the physiological and morphological characteristics of the *Eustoma* plant of claim 2.

6. A method for producing a *Eustoma* seed comprising crossing a first parent *Eustoma* plant with a second parent *Eustoma* plant and harvesting the resultant hybrid *Eustoma* seed, wherein said first or said second parent *Eustoma* plant is the *Eustoma* plant of claim 2.

7. A hybrid *Eustoma* seed produced by the method of claim 6, wherein the seed produces a *Eustoma* plant having a deformed pistil.

8. A hybrid *Eustoma* plant having a deformed pistil, or its parts, produced by growing said hybrid *Eustoma* seed of claim 7.

9. Tissue culture of the seed of claim 1.

10. A *Eustoma* plant regenerated from the tissue culture of claim 9, wherein said *Eustoma* plant expresses a deformed pistil.

11. Tissue culture of regenerable cells of the plant, or its parts, of claim 2.

12. The tissue culture of claim 11 wherein said regenerable cells are embryos, meristematic cells, pollen, leaves, anthers, roots, root tips, flowers, seeds, stems, buds or protoplasts or calli derived therefrom.

13. The tissue culture of claim 11 wherein said tissue culture is a pseudofertilized ovule culture.

14. The tissue culture of claim 11 wherein said tissue culture is a hyperploidy pollen culture.

15. The tissue culture of claim 11 wherein said tissue culture is an adventitious embryo culture.

16. The tissue culture of claim 11 wherein said tissue culture is a callus culture.

17. A *Eustoma* plant regenerated from the tissue culture of claim 11, wherein said *Eustoma* plant expresses a deformed pistil.

18. A progeny of the *Eustoma* seed of claim 1, said progeny having a deformed pistil.

19. The *Eustoma* plant of claim 2, said plant having a flowering period from 6% to 80% longer than that of a *Eustoma* plant of the same variety having a normal pistil.

20. A method for breeding a *Eustoma* plant, comprising artificially self-pollinating the *Eustoma* plant of claim 2.

21. A method for breeding a *Eustoma* plant having a deformed pistil, comprising crossing the *Eustoma* plant of claim 2 with a *Eustoma* plant not having a deformed pistil.

22. A method for breeding a *Eustoma* plant having a deformed pistil, comprising crossing a first *Eustoma* plant having a deformed pistil with a second *Eustoma* plant having a deformed pistil, wherein said first or said second *Eustoma* plant is the *Eustoma* plant of claim 2.

23. The progeny of the *Eustoma* seed of claim 18, said progeny having a flowering period from 6% to 80% longer than that of a *Eustoma* plant of the same variety having a normal pistil.

* * * * *